(12) United States Patent
Fegely et al.

(10) Patent No.: US 7,709,025 B2
(45) Date of Patent: May 4, 2010

(54) ENTERIC COATINGS FOR ORALLY INGESTIBLE SUBSTRATES

(75) Inventors: Kurt Fegely, Limerick, PA (US); Simon Tasker, Audubon, PA (US); Lawrence Martin, Glenside, PA (US)

(73) Assignee: BPSI Holdings, Inc., Wilmington, DE (US)

( * ) Notice: Subject to any disclaimer, the term of this patent is extended or adjusted under 35 U.S.C. 154(b) by 31 days.

(21) Appl. No.: 11/088,352

(22) Filed: Mar. 24, 2005

(65) Prior Publication Data

US 2005/0220878 A1    Oct. 6, 2005

Related U.S. Application Data

(60) Provisional application No. 60/557,934, filed on Mar. 31, 2004.

(51) Int. Cl.
*A61K 9/24* (2006.01)
(52) U.S. Cl. .................. 424/473; 514/57; 424/468
(58) Field of Classification Search .................. None
See application file for complete search history.

(56) References Cited

U.S. PATENT DOCUMENTS

| | | | |
|---|---|---|---|
| 4,123,403 A | 10/1978 | Warner et al. | |
| 4,308,251 A | 12/1981 | Dunn et al. | |
| 4,330,338 A | 5/1982 | Banker | |
| 4,502,888 A | 3/1985 | Leng et al. | |
| 5,284,659 A * | 2/1994 | Cherukuri et al. | 424/441 |
| 5,711,967 A * | 1/1998 | Juch | 424/462 |
| 5,840,293 A * | 11/1998 | Nacht et al. | 424/78.02 |
| 6,251,430 B1 * | 6/2001 | Zhang et al. | 424/468 |
| 6,365,148 B1 | 4/2002 | Kim et al. | |
| 6,420,473 B1 | 7/2002 | Chittamuru et al. | |
| 6,468,561 B1 * | 10/2002 | Grillo et al. | 424/480 |
| 6,703,044 B1 | 3/2004 | Pinhasi et al. | |
| 6,777,397 B2 * | 8/2004 | Zehner et al. | 514/53 |
| 2002/0098235 A1 | 7/2002 | Dittmar et al. | |
| 2002/0098242 A1 | 7/2002 | Darder | |
| 2002/0164371 A1 | 11/2002 | Ting et al. | |
| 2002/0187189 A1 | 12/2002 | Betageri | |
| 2003/0096002 A1 * | 5/2003 | Borek et al. | 424/452 |

FOREIGN PATENT DOCUMENTS

WO    WO 03/053402 A1    7/2003

OTHER PUBLICATIONS

Morales et al. Comparative study of morphine diffusion from sustained release polymeric suspensions. Journal of Controlled Release 95 (2004) 75-81. Accessed online on Mar. 6, 2008 at ScienceDirection.com.*
Aquacoat Brochure. FMC Biopolymer. p. 7. Accessed online on Mar. 6, 2008 at FMCBiopolymer.com.*
Aquacoat Brochure. FMC Biopolymer. pp. 1 and 7. Accessed online on Mar. 6, 2008 at FMCBiopolymer.com.*
Vijayalakshmi et al., Development of Aiginate Based Aqueous Film Coating Formula for Tablets, Indian Journal of Pharmaceutical Sciences, Feb. 2004 , pp. 125-129.*
Vijayalakshmi, et al., Development of alginate based aqueous film coating formula for tablets, Indian Journal of Pharmaceutical Sciences, 2000, 62(6): 125-129.

* cited by examiner

*Primary Examiner*—Yvonne L Eyler
*Assistant Examiner*—Suzanne Ziska
(74) *Attorney, Agent, or Firm*—Lucas & Mercanti, LLP

(57) ABSTRACT

Enteric film coating systems for orally ingestible substrates such as pharmaceutical tablets and dietary supplements are disclosed. In preferred aspects, the enteric film coatings include an ethylcellulose dispersion and a substantially gastro-insoluble pore former such as sodium alginate.

25 Claims, No Drawings

ENTERIC COATINGS FOR ORALLY INGESTIBLE SUBSTRATES

CROSS-REFERENCE TO RELATED APPLICATIONS

This application claims the benefit of priority from U.S. Provisional Patent Application Ser. No. 60/557,934 filed on Mar. 31, 2004, the contents of which are incorporated by reference herein.

BACKGROUND OF THE INVENTION

1. Field of the Invention

The field of this invention is enteric coatings for orally ingestible substrates such as pharmaceutical tablets and dietary supplements.

2. Description of the Prior Art

Within this field, there are already a number of enteric coating formulations that are useful, including Acryl-EZE® and Sureteric®, both manufactured and sold by the Assignee of present application. However, all of the components of currently marketed enteric coating formulations are not approved for use in food, nutritional supplements and pharmaceutical applications in every target market in the world. Furthermore, there is a continuing need in the food, nutritional supplements and pharmaceutical markets to develop novel, enteric-coated products that may allow pharmaceutical or nutritional supplements companies to positively differentiate themselves from competition.

A technical brochure entitled "Alginates for Pharmaceutical Applications"(Code: PHARM/ALG/0800), published by International Specialty Products, the disclosure of which is incorporated herein by reference, indicates that alginates such as sodium alginate have been used in some commercial tablet coating systems to achieve an enteric barrier in the stomach. It is further indicated that alginates are dissolved in water at the 5-10% level and that films with greater integrity are produced if a plasticizer, such as glycerine or propylene glycol, is incorporated. There is no disclosure or suggestion in the brochure, however, concerning how coating at a solids level greater than 10% in water, which would result in a faster coating process and an overall more economical operation, could be carried out. Furthermore, increasing the concentration of sodium alginate in water above 10% (w/w) will result in a solution viscosity that will make pumping and spraying the solution difficult or impossible.

U.S. Pat. No. 6,365,148 describes multiple systems capable of achieving an enteric effect when coated onto lactic acid bacteria granules. It is disclosed that a sodium alginate coating alone at a low temperature or in combination with a "controlled release" topcoat, which may be comprised of sodium alginate and/or ethylcellulose, may be used to impart an enteric effect. Nowhere is it stated that the controlled release (top coat) layer alone, nor the specific combination of ethylcellulose and sodium alginate by themselves in a single coating layer, could function as an effective enteric coating. Furthermore, the '148 patent discloses the use of a limited list of plasticizers that are not necessarily the most preferred for film-forming and organoleptic properties. For example, the '148 patent is silent regarding the use of dibutyl sebacate and medium chain triglycerides (also known as fractionated coconut oil).

In spite of the improvements provided in the art, there continues to be a need for improved enteric coating systems. The present invention addresses this need.

SUMMARY OF THE INVENTION

It is an object of this invention is to produce an enteric film coating system that has broad regulatory acceptance and can be applied to orally ingestible substrates in a highly productive manner. In accordance with this and other objects, one preferred aspect of the invention includes an enteric film coating system containing an aqueous ethylcellulose dispersion and a substantially gastro-insoluble pore former (i.e. insoluble in the stomach at a pH of about 1). In a preferred aspect of the invention, the ethylcellulose portion of the film coating system is provided by including Surelease®, a product of Colorcon, West Point, Pa., which is a formulated product containing an aqueous ethylcellulose dispersion and a plasticizer. A preferred substantially gastro-insoluble pore former is sodium alginate.

Additional aspects of the invention include methods of preparing the film coating systems described herein as well as orally ingestible substrates (tablets, caplets, etc.) coated with the inventive enteric coating system.

DETAILED DESCRIPTION OF THE INVENTION a) Ethylcellulose Portion of Dispersion In accordance with a first aspect of the invention, there is provided an enteric film coating system containing an ethylcellulose dispersion and a substantially gastro-insoluble pore former. The ethylcellulose dispersion of this invention is comprised of ethylcellulose, in a sub-micron to micron particle size range, usually ranging from about 0.1 to 10 microns in size, homogeneously suspended in water with the aid of an emulsification agent such as ammonium oleate. The ethylcellulose dispersion may optionally and preferably contain a plasticizer such as dibutyl sebacate or medium chain triglycerides. Such ethylcellulose dispersions may be manufactured according to U.S. Pat. No. 4,502,888, which is incorporated herein by reference. One such ethylcellulose dispersion product made according to the process disclosed in this patent is marketed under the trademark Surelease®, by Colorcon of West Point, Pa. In accordance with this embodiment, the ethylcellulose particles are blended with oleic acid and a plasticizer, then extruded and melted. The molten plasticized ethylcellulose is then directly emulsified in ammoniated water in a high shear mixing device under pressure. Ammonium oleate is formed in situ to stabilize and form the dispersion of plasticized ethylcellulose particles. Additional purified water is then added to achieve the final solids content. See also U.S. Pat. No. 4,123,403, which is incorporated herein by reference.

In an alternative aspect of the invention, the ethylcellulose dispersion can also be prepared by dissolving ethylcellulose in a water-immiscible organic solvent, emulsifying the organic solution in water, optionally with the aid of additives, and stripping the organic solvent from the suspension. This process is described in detail in U.S. Pat. No. 4,330,338, which is incorporated herein by reference. One such product made according to the process disclosed in this patent is Aquacoat® ECD and is available from FMC of Philadelphia, Pa. A plasticizer is not ordinarily incorporated in the ethylcellulose dispersions during this process; however, a plasticizer may optionally and preferably be added after the production of the dispersion is complete.

A non-limiting list of suitable plasticizers useful in the film coating systems of the present invention include alkyl esters of carboxylic acids, polypropylene glycol, castor oil, fractionated coconut oil, dibutyl sebacate, polyethylene glycol, propylene glycol, glycerine, triacetin, acetyltriethyl citrate, triethyl citrate, tributylcitrate, acetyltributylcitrate or mixtures thereof. Preferably, the plasticizer is dibutyl sebacate, medium chain triglycerides such as fractionated coconut oil, or mixtures thereof. The plasticizer can be present in amounts of up to about 30% of the ethylcellulose content of the film coating system of the present invention. Preferably, the plasticizer is present in amounts of from about 10% to about 25% of the ethylcellulose content, and more preferably from about 15% to about 25% of the ethylcellulose content of the film coating system.

The amount of ethylcellulose included in the film coating systems of the present invention will depend somewhat on the type selected, but for purposes of illustration and not limitation, the ethylcellulose concentration is usually from about 5% to 30%, with amounts of about 7.5 to 20% being most preferred.

b) Gastro-insoluble Pore Formers

The gastro-insoluble pore former included in the film coating systems of the present invention can be any art recognized pore forming chemical species that is compatible for use with ethylcellulose dispersions and is substantially insoluble at a pH below about 3, but is readily soluble at a pH of greater than about 5. Preferably, the gastro-insoluble pore former is sodium alginate. As an alternative to or in addition to sodium alginate, the film coating systems of the present invention can also include alginic acid or other alginates such as potassium alginate or other salts formed between deprotonated alginic acid and monovalent cations. Low viscosity grades of sodium alginate, especially those with solution viscosities of less than about 100 centipoise in 1% aqueous solutions, are preferred. Keltone® LVCR and Manucol® LB low viscosity sodium alginate grades, marketed by ISP, are particularly preferred.

The amount of gastro-insoluble pore former included in the film coating systems of the present invention will depend somewhat on the gastro-insoluble pore former selected, but for purposes of illustration and not limitation, the sodium alginate concentration is usually from about 0.5 to 10%, preferably from about 1.0 to 5.0%, with amounts of about 1.5-3.5% being most preferred.

c) Ratios of Ethylcellulose: Gastro-insoluble Pore Former

In most aspects of the invention, the ratio of ethylcellulose to gastro-insoluble pore former in the film coating systems range from about 1:1 to about 10:1. In preferred aspects, the ratio is from about 3.5:1 to about 6:1, while in more preferred aspects, it is about 4.25:1.

As mentioned previously, the preferred gastro-insoluble pore former is sodium alginate and a preferred source of ethylcellulose dispersion is Surelease. An example of one inventive film coating system including these two components will actually contain a preferred ratio of the non-water components of Surelease (nominally 25% solids) to sodium alginate of 85:15 (w/w). Since the non-water ingredients of Surelease are comprised of about 75% ethylcellulose, the preferred ratio of ethylcellulose to sodium alginate is 63.75:15 or about 4.25 to 1 (w/w). For the purposes of this description, "solids" means all non-water ingredients, including potentially plasticizers, that exist in the liquid state when pure.

d) Preferred Dispersion Solids Levels

Surelease is supplied as a 25% solids dispersion, and, in this invention, is mixed with an aqueous solution containing an appropriate amount of sodium alginate in order to provide the ratios described above. In preferred aspects of the invention, the ultimate % solids levels of the inventive dispersions are as high as possible without increasing the dispersion viscosity to a point where the dispersion becomes to difficult to process. As will be appreciated by those of ordinary skill, one begins to encounter difficulties spraying dispersions (regardless of content) when the viscosity is greater than about 2,000 centipoise (cps). Thus, the viscosity of the final film coating systems or dispersions of the present invention is less than about 2,000 cps. Preferably, dispersion viscosities are in the range of about 100 to about 1,000 cps. Viscosity exponentially increases with increasing amounts of sodium alginate in the dispersion. Therefore, it is important that the sodium alginate content and overall solids levels be carefully monitored to stay within the ranges described herein. Dispersions with viscosities lower than 100 centipoise are processible; however, these dispersions would likely have low total solids levels, which would be disadvantageous from a coating process time standpoint. Preferably, the inventive dispersions will be applied onto tablets or tablet cores at an overall solids level of not less than 10% while maintaining the ethylcellulose to sodium alginate ratio in the preferred range of 1:1 to 10:1. Generally, film coating systems of the present invention are applied at an overall solids level of from about 10 to about 20%, with levels of about 15.0% being more preferred.

e) Auxiliary Ingredients

The enteric film coating system may contain a number of additives that are common in the film coating arts. These include surfactants, emulsifiers, detackifiers, flow aids, flavorants, colorants, etc. and mixtures thereof.

The surfactants or emulsifiers assist in producing a stable emulsion. The emulsifiers may be anionic such as sodium lauryl sulfate (USP), cationic such as the quaternary ammonium halides (such as cetyl pyridinium chloride) or non-ionic, such as linear fatty alcohol ethoxylatesor the polyoxyethylene condensation products (exemplified by Spans and Tweens or polyoxyethylenepolypropylene glycol as Pluronic F68, available from BASF Corp., Mt. Olive, N.J.). Other agents including materials such as polyglycerol esters of fatty acids, polyoxyethylene sorbitan monolaurate, polyoxethylene sorbitan tristearate, polyoxethylene sorbitan monostearate, polyoxyethylene sorbitan monoleate, propylene glycol mono and diesters of fats and fatty acids, sodium lauryl sulfate and sorbitan monostearate are useful to serve such functions. Generally, the emulsions and latices of the instant invention can be formed without surfactants or emulsifiers, but in many instances, finer particle size and greater stability are attained with such additives. The particular above-listed bio-degradable polymers form emulsions and resulting latices without benefit of additives.

Various other additives, such as cetyl alcohol, beeswax, (yellow, bleached or white and white natural), candelilla wax, carnauba wax, cocoa butter, fatty acids such as stearic acid, mono, di and tri glycerides (including glyceryl monostearate, monooleate, etc. and self-emulsifying glyceryl monostearate), glycerol-lacto stearate, oleate or palmitate (other self emulsifying waxes), glyceryl-lacto esters of fatty acids (also self emulsifying) lauric acid, lauryl alcohol, linoleic acid, octyl alcohol and acetate, and paraffin may be advantageously included to enhance the properties of the dispersion. A number of additives such as carnauba wax and chlorowax improve the appearance of the tablet coating. These, of course, can be added to the system as polishing agents The emulsifier or surfactant makes up from about 0.1% to 10% by weight of the film coating system. More preferably, the emulsifier is from about 0.3% to 6% by weight of the system, while most preferably, it is from 0.5% to about 3.5% by weight.

The flavorant(s), which is used primarily for taste- and/or odor-masking, may be vanillin, sodium citrate, citric acid, mint, orange, lemon oil, or any other pharmaceutically approved flavorant or taste-masking agent, and combinations thereof.

The colorants may be FD&C and D&C lakes, titanium dioxide, iron oxides, natural pigments, pearlescent pigments or dyes approved for ingestion by the U.S. Federal Drug Administration, or combinations thereof. Preferably, the colorant comprises from about 0.01% to about 30% by weight of the system. For Surelease containing systems, the colorant should be any colorant described above which is stable at the pH of the dispersion (about 10).

g) Methods of Making Film Coating Systems—Dispersions

In accordance with another aspect of the invention, there is provided a method of preparing the inventive film coating systems. The methods include providing or preparing an aqueous dispersion of ethylcellulose particles having the size distribution mentioned above and combining this dispersion with a solution containing the gastro-insoluble pore former. The mixture is combined with a suitable mixer such as a propeller mixer until a substantially homogeneous dispersion is obtained. In a preferred aspect of the invention, the inventive enteric dispersion is prepared in the following manner: a solution containing the gastro-insoluble pore former, sodium alginate, is prepared by adding a suitable sodium alginate such as Manucol LB into a suitable quantity of distilled water to form about a 5% solution and stirring this combination with a propeller mixer for a sufficient time until the sodium alginate is completely dissolved and uniformly dispersed in the water. To this solution, Surelease brand fully formulated ethylcellulose dispersion containing a plasticizer is added. The resulting dispersion is mixed gently for a sufficient time until a uniform coating dispersion is obtained, preferably having about a 10-20% solids content and a viscosity of between 100-2,000 centipoise (Brookfield viscometer, spindle 2, 20 r.p.m.) at room temperature.

Auxiliary ingredients may be added in a number of ways. First, the auxiliary ingredients may be added to the gatro-insoluble pore former before dispersion in water. In this case, the auxiliary ingredients are preferably preblended with the gastro-insoluble pore former to obtain a homogeneous mixture before addition to water. Second, the auxiliary ingredients may be added sequentially to a stirred dispersion of the gastro-insoluble pore former in water, insuring that the auxiliary ingredients are homogeneously dispersed before the ethyl cellulose dispersion is added. Third, the auxiliary ingredients may be added to the ethyl cellulose dispersion taking care that the auxiliary ingredients are homogeneously dispersed prior to the addition to the dispersion of the gastro-insoluble pore former in water. Fourth and finally, the auxiliary ingredients may be added to a mixture of the gastro-insoluble pore former and ethylcellulose dispersions after these two dispersions are mixed. Again, care must be exercised to insure all components are homogeneously mixed.

h) Method of Application to Tablet Cores

In accordance with another aspect of the invention, there is provided a method of coating orally-ingestible substrates with the enteric film coating systems described herein. The methods include applying the enteric film coating systems described herein to a substrate such as an orally-ingestible substrate. A non-limiting list of suitable substrates which can be coated with the inventive coating system include compressed tablets, caplets, cores including pharmaceuticals, nutraceuticals and dietary supplements as well as any other art-recognized orally ingestible core. Garlic tablets and soft gelatin capsules containing fish oil are examples of suitable orally ingestible substrates. Preferably, the enteric film coating system is applied to the tablet or other core until a weight gain of from about 0.5% to about 20% is achieved. More preferably, the weight gain is from about 2% to about 10% while most preferably, the weight gain is from about 4% to about 8%. The coating is preferably applied using any art recognized method of coating pharmaceutical tablets or multiparticulates.

In other aspects of the invention, the tablet cores are coated with a sealing coat to a weight gain of up to about 3% by weight before the inventive enteric coatings are applied. The purpose of the sealing coat is to improve the mechanical strength of the tablet core and serve as a barrier layer between the substrate and topcoat to prevent potential interactions between the substrate and enteric topcoat. Suitable sealing coatings include those that do not substantially delay the release of the active ingredient formulated in the core. A non-limiting list of such immediate release film coating systems are Opadry®, Opadry II, Opadry NS and Opaglos® 2, which are available from Colorcon.

EXAMPLES

The following examples serve to provide further appreciation of the invention but are not meant in any way to restrict the effective scope of the invention.

The following materials were used in the examples of this invention:

| Material | Function | Supplier |
|---|---|---|
| Surelease ® (ethylcellulose content: 18.8%) (medium chain triglycerides content: 40%, 21.3% wrt ethylcellulose) (25% solids w/w) | Film former | Colorcon |
| Sodium Alginate | Film/pore former | ISP Alginates |
| a) Manucol LB | 1% solution = 4 cP | |
| b) Keltone LVCR | 1% solution = 50 cP | |
| Opadry ® NS Clear | Film former/seal layer | Colorcon |
| Opadry ® Clear | Film/pore former | Colorcon |

Tablet Cores

Garlic Core A—11.2 millimeter standard concave round (545 milligram total weight)

Garlic Core B—19.2-millimeter caplet (875 milligram total weight)

Example 1 a) Composition of Matter

Garlic cores (1.0 Kg total charge Core A) were coated sequentially with a seal-coating dispersion made from a Opadry® NS Clear coating composition, and an enteric coating dispersion comprised of the inventive composition.

First, the Opadry NS seal-coating dispersion was prepared by adding the Opadry NS formula (30 grams) to distilled water (345 grams) and stirring this combination for 45 minutes with a propeller mixer. The resultant dispersion was homogenous with a yellowish-brown hue. Coating of this dispersion onto the tablets resulted in a theoretical weight gain of 30 grams/1,000 grams or 3%.

The inventive enteric dispersion was prepared in the following manner. The sodium alginate solution was prepared by adding Manucol LB (12 grams) to distilled water (249.33 grams) and stirring this combination with a propeller mixer for 45 minutes. The resultant solution was opaque with a yellowish-brown hue. To this solution was added Surelease (272 grams), and the resulting dispersion was mixed gently for 30 minutes with a propeller mixer. Since Surelease contains 25% (w/w) non-water or "dry" ingredients, the amount of non-water ingredients contributed by the Surelease dispersion to the resultant mixture was 68 grams. Therefore, the relative ratio of non-water Surelease components to sodium alginate was 68:12 grams or 85% to 15% (w/w). The final coating dispersion had a dispersion solids content of 80 grams of non-water ingredients in 533.33 grams of total coating dispersion or, about 15% solids. The final coating dispersion was opaque and off-white in color and maintained a viscosity of 378 centipoise (Brookfield viscometer, spindle 2, 20 r.p.m.) at room temperature.

b) Method Of Application

To a fully-perforated, side vented coating pan (1 kilogram capacity) equipped with a Cole-Parmer Masterflex pump with one pump head, silicone tubing, and one air assisted spraying nozzle, were added garlic cores (Garlic Core A, 1.0 kg charge). The cores were sequentially coated with the Opadry NS seal layer (3% theoretical weight gain, 8% solids) and the inventive coating dispersion under the following process conditions:

c) Coating Parameters—Seal and Enteric Layer

| Parameter | Seal-Layer | Enteric Layer |
| --- | --- | --- |
| Inlet Temperature (° C.) | 57 | 57 |
| Exhaust Temperature (° C.) | 44 | 44 |
| Product Temperature (° C.) | 43 | 41 |
| Fluid Delivery Rate (g/min.) | 12 | 12 |
| Atomization pressure (psi) | 25 | 30 |
| Pattern Air Pressure (psi) | 25 | 30 |
| Drying Air Volume (cfm) | 120 | 120 |
| Pan rotational speed (rpm) | 15 | 16 |
| Process Time (minutes) | 28 | 37 |

Samples were removed from the coating pan at 4, 6, and 8 percent weight gains of the enteric layer for analysis.

d) Method of Analysis

Six tablets were subjected to disintegration analysis in hydrochloric acid (0.1 N) for one hour. After this interval, the tablets were removed from the disintegration tank and examined for evidence of cracking, peeling, bloating, or film rupture. Results identified as "PASS" represent that the six tablets did not exhibit cracking, peeling, bloating, or film rupture.

Following testing in 0.1N HCl, the tablets were placed directly into pH 6.8 phosphate buffer and measured for disintegration time. The results listed are the average times required for complete disintegration of the garlic core.

Disintegration Results—Example 1

| Theoretical Weight Gain | Enteric Disintegration | pH 6.8 Buffer Disintegration Time (min:sec) |
| --- | --- | --- |
| Garlic Core A | Not applicable | 40:42 +/− 5:14 |
| 4% | PASS | 71:54 +/− 13:48 |
| 6% | PASS | 87:30 +/− 8:30 |
| 8% | PASS | 95:30 +/− 4:52 |

Examples 2-4

Examples 2-4 are inventive compositions prepared in a manner analogous to the method described in Example 1 with slight adjustments to the composition or method of application, as outlined in the following table.

In Examples 2-4, the appearance and texture of the finished dosage form were similar in nature to that of Example 1. Differences were noted in Example 2, wherein, at a ratio of 75/25 Surelease solids to sodium alginate, a higher weight gain of the enteric layer was required to achieve enteric protection. In addition, the higher sodium alginate content provided faster disintegration times in pH 6.8 buffer at an equivalent weight gain compared to Example 1.

Examples 3-4 indicate that higher viscosity and, therefore, higher molecular weight grades of sodium alginate may be used successfully in the inventive compositions; however, the use of the higher viscosity grades requires that the dispersions be prepared at lower solids content to insure that they may be of sufficiently low viscosity to be readily sprayed onto tablets.

Comparative Data Table—Examples 2-4

| | Weight in Grams in Dispersion | | |
| --- | --- | --- | --- |
| Components | Example 2 | Example 3 | Example 4 |
| Surelease (same as Example 1) | 240 | 272 | 272 |
| Keltone LVCR Sodium Alginate 50 cP | | 12 | 12 |
| Manucol LB Sodium Alginate 4 cP | 20 | | |
| Additional Water | 273.3 | 356.0 | 356.0 |
| Dispersion Total (grams) | 533.3 | 640 | 640 |
| Core Type | | | |
| Garlic Core A | X | | |
| Garlic Core B | | X | X |
| Seal Coat (If applicable) | | | |
| Opadry NS Clear | X | X | |
| Dry Solids Content (%) | 15% | 12.5% | 12.5% |
| Dispersion Viscosity (cP) | 690 | 1550 | 1550 |

Disintegration Results—Examples 2-4

| Theoretical Weight Gain | Enteric Disintegration | pH 6.8 Buffer Disintegration Time (min:sec) |
| --- | --- | --- |
| Garlic Core B | Not applicable | 55:12 |
| Example 2 - 8% | PASS | 62:00 +/− 4:34 |
| Example 3 - 4% | PASS | 98:12 +/− 5:57 |
| Example 4 - 4% | PASS | 97:24 +/− 8:17 |

Examples 5-6

Examples 5-6 are comparative compositions and dispersions prepared in a manner analogous to the method described in Example 1 with slight adjustments to the composition or method of application, as outlined in the following table.

In Examples 5-6, differences were noted in the disintegration times in pH 6.8 buffers. Inclusion of Opadry Clear into the enteric film coating system significantly increased the disintegration times to the point where these coated dosage forms would not be considered suitable for human consumption. This indicates that sodium alginate creates pores through which the surrounding medium or an active ingredient may migrate much more effectively than a film coating system based on hypromellose does.

Comparative Data Table—Examples 5-6

| Components | Weight in Grams in Dispersion | |
|---|---|---|
| | Example 5 | Example 6 |
| Surelease E-7-19010 (same as Example 1) | 272 | 272 |
| Opadry Clear | 12 | 12 |
| Additional Water | 516 | 516 |
| Dispersion Total (grams) | 800 | 800 |
| Core Type | | |
| Garlic Core B | X | X |
| Seal Coat (If applicable) | | |
| Opadry NS Clear | | X |
| Dry Solids Content (%) | 10% | 10% |
| Dispersion Viscosity (cP) | 44 | 44 |

Disintegration Results—Examples 5-6

| Theoretical Weight Gain | Enteric Disintegration | pH 6.8 Buffer Disintegration Time (min:sec) |
|---|---|---|
| Example 5 - 4% | PASS | >300 minutes |
| Example 6 - 4% | PASS | >300 minutes |

We claim:

1. An enteric film coating dispersion comprising:
a film coating amount of ethylcellulose particles;
water and optionally a water-immiscible organic solvent for dispersing the ethylcellulose; and
a substantially gastro-insoluble pore former comprising a salt formed between deprotonated alginic acid and monovalent cations;
wherein the ratio of ethylcellulose in said ethylcellulose dispersion to gastro-insoluble pore former is from about 3.5:1 to about 6:1 whereby when coated onto an orally-ingestible substrate, said substrate is substantially insoluble in a medium of 0.1 N HCl for one hour.

2. The enteric film coating dispersion of claim 1, wherein said substantially gastro-insoluble pore former is sodium alginate.

3. The enteric film coating dispersion of claim 1, wherein said ratio of ethylcellulose in said ethylcellulose dispersion to gastro-insoluble pore former is about 4.25:1.

4. The enteric film coating dispersion of claim 1, wherein the ethylcellulose dispersion comprises plasticized ethylcellulose particles.

5. The enteric film coating dispersion of claim 1, further comprising a plasticizer.

6. The enteric film coating dispersion of claim 5, wherein the plasticizer is selected from the group consisting of dibutyl sebacate, medium chain triglycerides, and mixtures thereof.

7. The enteric film coaling dispersion of claim 5, wherein the plasticizer is present in an amount up to about 30% of the amount of ethylceilulose.

8. The enteric film coating dispersion of claim 7, wherein the plasticizer is present in an amount of from about 15 to about 25% of the amount of ethylcellulose.

9. The enteric film coating dispersion of claim 1, wherein the viscosity is less than about 2,000 centipoise.

10. The enteric film coating dispersion of claim 9, wherein the viscosity is from about 100 to about 1,000 centipoise.

11. The enteric film coating dispersion of claim 2, wherein the sodium alginate concentration is from about 0.5 to about 10%.

12. The enteric film coating dispersion of claim 11, wherein the sodium alginate concentration is from about 1.0 to about 5.0%.

13. The enteric film coaling dispersion of claim 12, wherein said sodium alginate concentration is about 1.5 to about 3.5%.

14. The enteric film coating dispersion of claim 1, wherein the overall solids level is from about 10 to about 20%.

15. The enteric film coating dispersion of claim 1, further comprising a member of the group consisting of emulsifiers, detackifiers, surfactants, flow aids, flavorants, colorants and mixtures thereof.

16. An orally-ingestible substrate coated with the enteric film coating dispersion of claim 1.

17. The orally-ingestible substrate of claim 16 further comprising a sealing coating.

18. The orally-ingestible substrate of claim 16, wherein said enteric film coating dispersion is applied in an amount from about 0.5 to about 20% weight gain.

19. The orally-ingestible substrate of claim 18, wherein said enteric film coating dispersion is applied in an amount from about 4 to about 8% weight gain.

20. A method of coating orally-ingestible substrates with an enteric film coating, comprising applying the enteric film coating dispersion of claim 1 to orally-ingestible substrate.

21. The method of claim 20, further comprising the step of applying a sealing coating prior to applying the enteric film coating dispersion.

22. An enteric film coating dispersion comprising
a film coating amount of ethylcellulose;
water and, optionally, a water-immiscible organic solvent for dispersing the ethylcellulose;
a substantially gastro-insoluble pore former comprising a salt formed between deprotonated alginic acid and monovalent cations; wherein the ratio of ethylcellulose dispersion to gastro-insoluble pore former is from about 3.5:1 to about 6:1,
a plasticizer;
a member selected from the group consisting of emulsifiers, detackifiers, surfactants, flow aids, flavorants, colorants and mixtures thereof,
whereby when coated onto an orally-ingestible substrate said substrate is substantially insoluble in a medium of 0.1 N HCl for one hour.

23. An orally-ingestible substrate coated with the enteric film coating dispersion of claim 22 wherein the substrate is substantially insoluble in a medium of 0.1 N HCl for one hour.

24. An orally-ingestible substrate coated with the enteric film coating dispersion of claim 1, wherein the substrate is substantially insoluble in a medium of 0.1 N HCl for one hour.

25. The enteric film coating dispersion of claim 1, wherein said substrate coated with said enteric film coating dispersion disintegrates in a medium of about pH 6.8.

* * * * *